US005748750A

United States Patent [19]

L'Espérance et al.

[11] Patent Number: 5,748,750

[45] Date of Patent: May 5, 1998

[54] METHOD AND APPARATUS FOR ACTIVE NOISE CONTROL OF HIGH ORDER MODES IN DUCTS

[75] Inventors: André L'Espérance; Martin Bouchard; Bruno Paillard, all of Sherbrooke, Canada; Catherine Guigou, Christiansburg, Va.

[73] Assignee: Alumax Inc., Atlanta, Ga.

[21] Appl. No.: 872,397

[22] Filed: Jun. 10, 1997

Related U.S. Application Data

[63] Continuation of Ser. No. 498,064, Jul. 5, 1995, abandoned.

[51] Int. Cl.[6] .......... A61F 11/06

[52] U.S. Cl. .......... 381/71.5; 381/71.1

[58] Field of Search .......... 415/119; 381/73.1, 381/71.5, 71.1, 71.2, 71.7, 71.8, 94.1

[56] References Cited

U.S. PATENT DOCUMENTS

| | | | |
|---|---|---|---|
| 5,343,713 | 9/1994 | Okabe et al. | 381/71 |
| 5,511,127 | 4/1996 | Warnaka | 381/71 |

FOREIGN PATENT DOCUMENTS

| | | |
|---|---|---|
| 1088871 | 11/1980 | Canada . |
| 1161766 | 2/1984 | Canada . |
| 2074951 | 8/1991 | Canada . |
| 2082671 | 10/1992 | Canada . |
| 2082890 | 5/1993 | Canada . |
| 2142014 | 3/1994 | Canada . |
| 2041477 | 9/1996 | Canada . |
| 2082086 | 9/1996 | Canada . |
| 2065913 | 1/1997 | Canada . |

OTHER PUBLICATIONS

"Vector Quantization in Speech Coding" by John Mahoul, Salim Roucos, and Herbert Gish, *Proceedings of the IEEE*, vol. 73, No. 77, Nov., 1985, pp. 1551–1557.

"Development of an Active Acoustic Sink (AAS) for Noise Control Applications" by Clark J. Radcliffe, Sachin D. Gogate, and Greg Hall, *Active Control of Vibration and Noise (ASME)*, DE–vol. 75, 1994, pp. 43–50.

"Active Control of Noise Including Higher–Order Acousic Modes Propragating in a Duct" by T. Morishita, C. Yamaguchi, T. Tanaka, M. Taki, and T. Mori, *Inter–noise 94*, Aug. 29–31, pp. 1372–1376.

"Experimental Modeling of Acoustic Enclosures for Feedback Control Purposes" by David A. Naastad and A. Reza Kashani, *Active Control of Vibration and Noise (ASME)*, DE–vol. 75, 1994, pp. 25–33.

*Primary Examiner*—Curtis Kuntz
*Assistant Examiner*—Vivian Chang
*Attorney, Agent, or Firm*—Jones & Askew, LLP

[57] ABSTRACT

An active noise control system for effective control of higher order modes of noise propagation within a duct is disclosed. A plurality of error sensors is disposed within an error sensors plane, which plane is perpendicular to the longitudinal axis of the duct. The disclosed process and apparatus minimizes the mean square distance between the points of the area associated to each error sensor. The resulting arrangement of errors sensors optimizes the overall area that the error sensors can control and consequently the global efficiency of the controlling system.

12 Claims, 4 Drawing Sheets

| Arrangement of sensors | Number of error sensors | Error sensor in center? | 1st Perimeter of error sensors | | 2nd Perimeter of error sensors | | Ratio of $D_{MAX}/R_0$ |
|---|---|---|---|---|---|---|---|
| | | | $R/R_0$ | $\Delta\phi$ | $R/R_0$ | $\Delta\phi$ | |
|  | 3 | No | 0.55 | 120° | – | – | 0.85 |
|  | 4 | No | 0.60 | 90° | – | – | 0.69 |
|  | 5 | No | 0.62 | 72° | – | – | 0.61 |
|  | 6 | Yes | 0.69 | 72° | – | – | 0.56 |
|  | 7 | Yes | 0.70 | 60° | – | – | 0.51 |
|  | 8 | Yes | 0.70 | 51° | – | – | 0.46 |
|  | 9 | Yes | 0.71 | 45° | – | – | 0.44 |
|  | 10 | Yes | 0.71 | 40° | – | – | 0.41 |
|  | 11 | Yes | 0.73 | 36° | – | – | 0.375 |
|  | 14 | No | 0.33 | 4 x 36° | 0.75 | 45° + 4x90° | 0.344 |

METHOD AND APPARATUS FOR ACTIVE NOISE CONTROL OF HIGH ORDER MODES IN DUCTS

This is a continuation of U.S. patent application Ser. No. 08/498,064, filed Jul. 5, 1995, now abandoned.

TECHNICAL FIELD

The present invention relates generally to methods and apparatus for controlling noise, and relates more specifically to a method and apparatus for active noise control of high order modes in ducts.

BACKGROUND OF THE INVENTION

Ducts are often a significant source of noise pollution in industrial environments. Examples of such ducts are smokestacks, scrubbers, baghouses, and the like. Because of increased anti-noise regulations, control of noise emanating from such ducts is not only desirable but also necessary.

Passive noise control measures, such as silencers, stack-stuffers, and the like suffer significant drawbacks. Such measures often require major stack structure redesign. In addition, passive measures impose significant penalties in terms of blower efficiency; usually the power of the blowers must be increased. Finally, known passive measures increase maintenance demands.

Thus there is a need for a noise control apparatus which does not require major stack structure redesign.

There is a further need for a noise control apparatus which does not impose significant performance penalties on blowers.

There is still a further need for a noise control apparatus which requires minimal maintenance.

In the case of plane wave propagation, active noise control has been successfully applied to reduce the acoustical energy emitted at the end of ducts. When higher order modes propagate in a duct, multi-channel noise control systems have to be used, and effective attenuation is more difficult to obtain.

Applicant is aware of only a very few studies related to the control of higher order modes in circular ducts. In fact, most of the studies were related to cases where only the plane mode and the first propagating mode were considered. One of the most recent studies related to the control of higher order modes in ducts have been presented by Morishita et al. In this study, the first four propagating modes in a square duct have been controlled, i.e., modes (0,0), (0,1), (1,0) and (1,1). In a square duct, the propagation modes are symmetric and fixed, which gives a relatively simple sound field, namely for propagating mode less or equal to the mode (1,1). However, in a circular duct, most frequently in reality, radial and circumferential rotational modes appear, which create a relatively complex sound field. This complexity may explain why, to the best of applicant's knowledge, no experimental results of active noise control system of higher order modes in circular ducts have been published in literature.

Thus there is a need for an active noise control system which provides suitable attenuation of higher order modes in circular ducts.

SUMMARY OF THE INVENTION

Stated generally, the present invention comprises a noise control system which does not require major stack structure redesign, does not impose significant penalties in terms of blower efficiency, and does not unduly increase maintenance demands. The noise control system attenuates higher order modes of propagation and is applicable to any shape of duct, whether round, rectangular, triangular, or other shape.

Stated somewhat more specifically, the present invention comprises an active noise control system for controlling high-order noise in ducts wherein a plurality of error sensors are disposed in an error sensors plane which is perpendicular to the longitudinal axis of the duct. Each of the plurality of error sensors is used as an input to a multiple-input, multiple-output controller.

According to one aspect of the invention, the error sensors are arranged such that the maximum distance between each error sensor and the boundary of the area under the influence of that error sensor is less than or equal to approximately one-third of the wavelength of the noise sought to be attenuated. The minimum number of error sensors needed and their locations in the error sensors plane is thus a function of the higher frequencies to be controlled and the size and shape of the duct.

Using the error sensors plane arrangement, and particularly with the number and location of the error sensors in the plane optimized according to the disclosed algorithm, noise reduction can be obtained for any type of noise (pure tone or wide band noise) in any shape of duct, subject only to the limitations of controller technology.

Thus it is an object of the present invention to provide an improved noise control apparatus.

It is another object of the present invention to provide a noise control system which is suitable for use within ducts of any cross-sectional shape.

It is still another object of the present invention to provide a noise control apparatus which is suitable for use within circular ducts.

Yet another object of the present invention is to provide a noise control apparatus which controls higher order modes of soundwave propagation within a duct.

Still another object of the present invention is to provide a noise control apparatus which does not require structural redesign or modification of the duct.

It is another object of the present invention to provide a noise control apparatus which will not extract a significant penalty in terms of blower efficiency.

Other objects, features, and advantages of the present invention will become apparent upon reading the following specification, when taken in conjunction with the drawings and the appended claims.

DETAILED DESCRIPTION OF THE DISCLOSED EMBODIMENT

Figure 1:
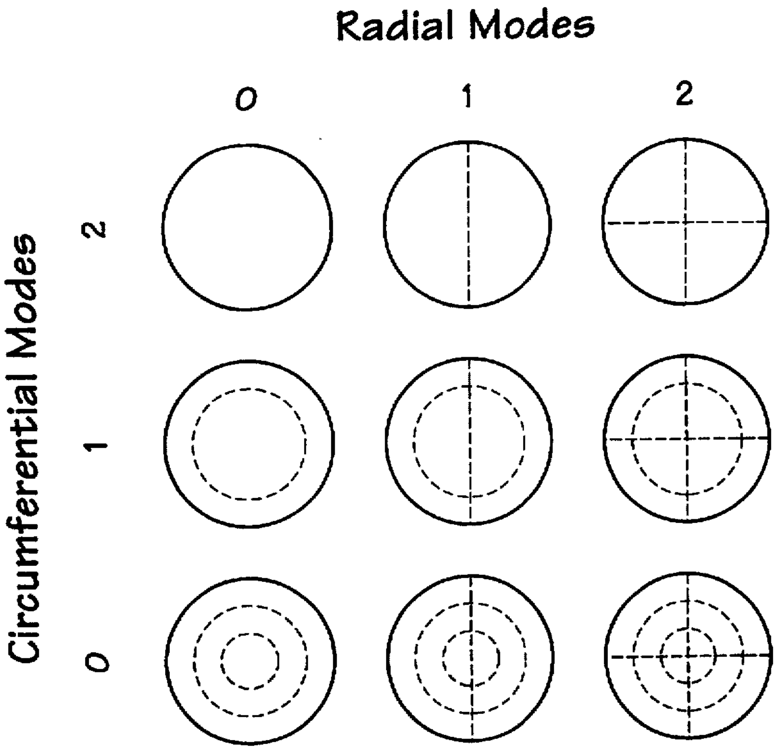
FIG. 1 is a chart illustrating nodal lines in a circular duct for the modes mn for m=0, 1, 2 and n=0,1,2.

Referring now to the drawings, like numerals will indicate like elements throughout the several views. The active noise control system which will be disclosed was developed to address the noise radiated by an industrial chimney 30 meters high and 1.8 meters in diameter. The noise radiated by the chimney is created by two fans located at its bottom which generate a pure tone of 320 Hz. The operating temperature within the chimney being 80° C., five modes propagate at this frequency in the chimney: (0,0),(1,0),(2,0),(0,1) and (3,0). FIG. 1 shows the nodal lines in a circular section for the modes mn when m=0, 1, 2 and n=0, 1,2.

Figure 2:
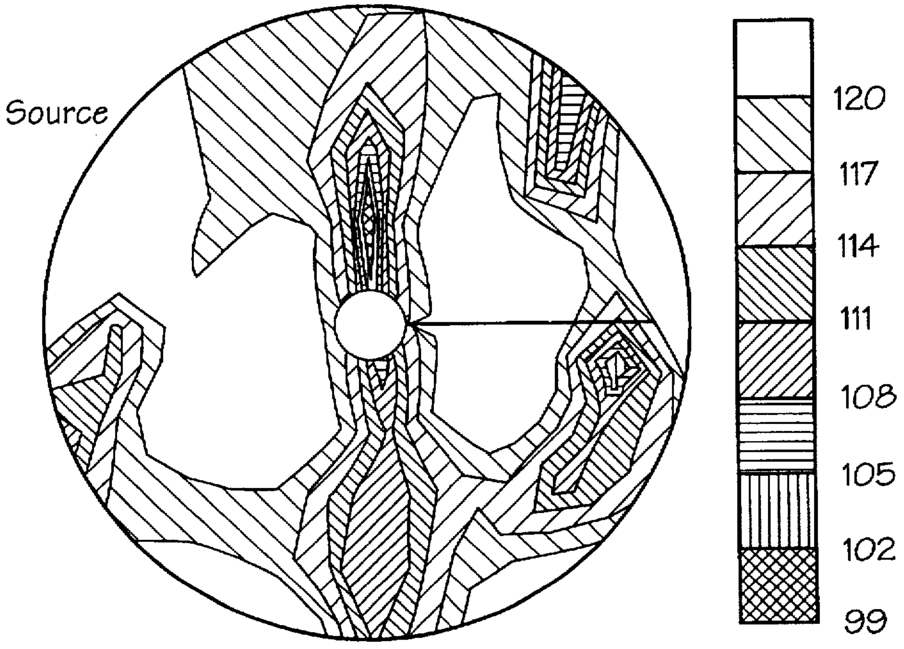
FIG. 2 is a graph showing the variations in sound pressure levels across a cross-section of a duct.

In a circular duct, radial modes can rotate and thus change the location of the modal lines along the duct. Therefore the sound field in a circular duct can be quite complex. FIG. 2 illustrates the sound field at 320 Hz in a cross section of a circular duct 1.8 meters in diameter.

Figure 3:
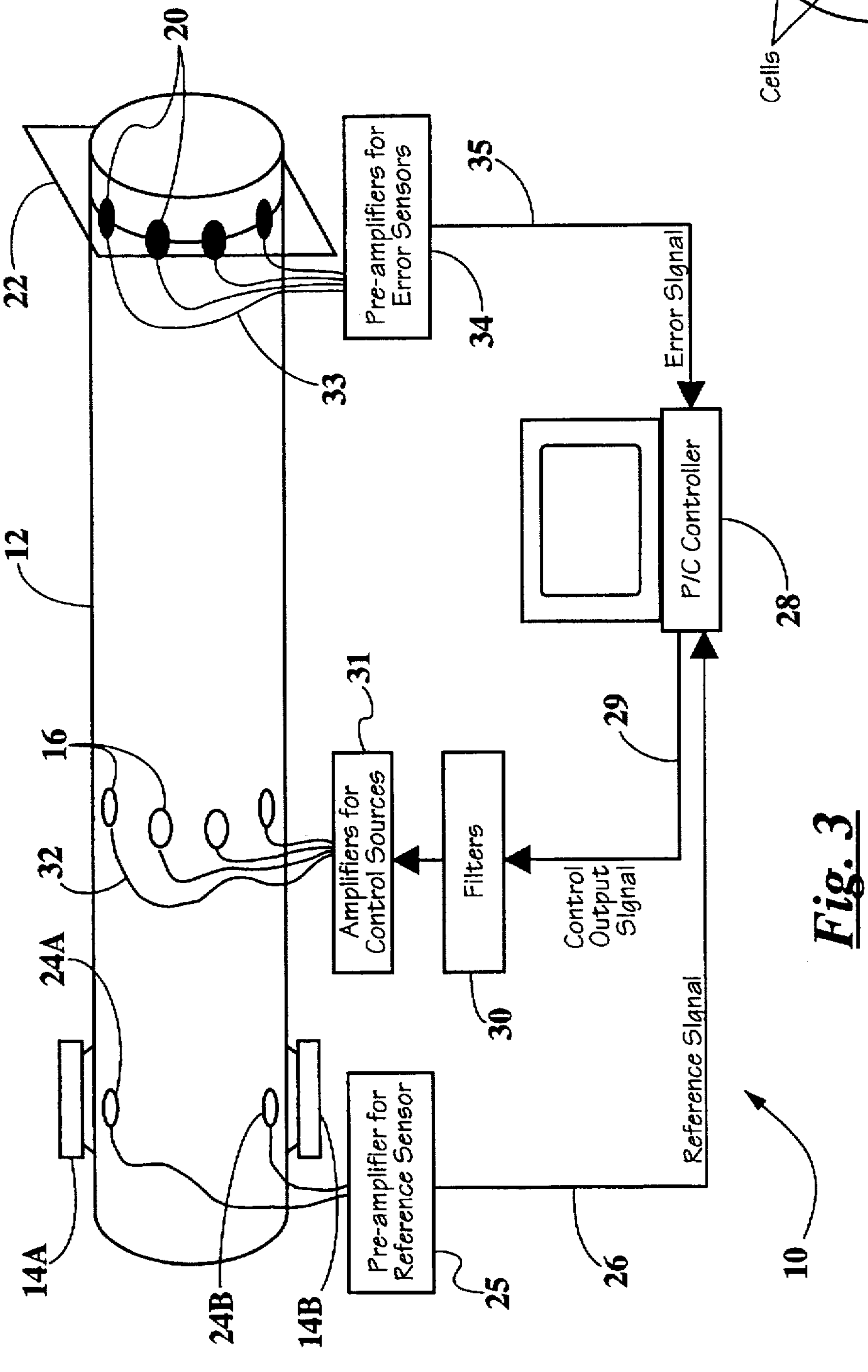
FIG. 3 is a schematic representation of an active noise control apparatus according to the present invention for attenuating noise within a circular duct.

FIG. 3 illustrates an active noise control system 10 of the disclosed embodiment. A circular duct 12 has a pair of primary noise sources 14A, 14B (the aforementioned twin fans) located at or near one end. The active noise control system 10 comprises a plurality of control sources, also referred to as actuators or speakers 16. The speakers 16 are arranged to transmit sound into the duct 12. In the embodiment shown in FIG. 3, the speakers 16 are located upstream of the primary noise sources 14A, 14B. The active noise control system 10 farther comprises a plurality of error sensors, or microphones 20. The microphones 20 are disposed within the duct 12 in a common plane hereinafter referred to as the "error sensors plane" 22, which plane is transverse to the longitudinal axis of the duct 12.

The active noise control system 10 further includes a pair of reference sensors 24A, 24B. The reference sensors 24A, 24B of the disclosed embodiment comprise optical sensors, one for each of the fans which comprise the noise sources 14A, 14B, which sensors detect the rotational speed of the fans. However, it will be appreciated that the reference sensors 24 are not limited to optical sensors but may comprise other types of sensors, such as a microphone positioned adjacent each primary noise source. Signals from each of the reference sensors 24A, 24B representative of the noise generated by the fans are input into a pre-amplifier 25, and the signal is sent via a signal path 26 to a PC controller 28.

A control output signal from the controller 28 is sent via a signal path 29 to a set of filters 30, as will be more fully explained hereinbelow. The filtered signal is then passed to an amplifier 31. The amplified output signal is transmitted from the amplifier 31 to the speakers 16 via signal paths 32. Similarly, the output signal from the microphones 20 is sent via signal paths 33 to a pre-amplifier 34, and the output signal from the pre-amplifier 33 is sent via a signal path 35 to be input into the controller 28.

The controller 28 of the disclosed embodiment is a conventional multichannel controller. Such controllers are commercially available from Digisonix, Inc., Technofirst, the University of Sherbrooke, and other sources. Commercial controllers often employ a widely used algorithm for real-time implementations of multichannel active control systems, known as the multi-channel Filtered-X LMS algorithm. The multi-channel Filtered-X LMS algorithm is based on the well-known Least Mean Square (LMS) algorithm, and retains most of its properties. Its convergence behavior is well understood. It is the simplicity of its structure and its low computational complexity that make it applicable to many real situations, using commercially available digital signal processors.

It will be understood that the controller 28 per se is of conventional design and thus will not be explained in great detail. To explain the multi-channel Filtered-X LMS algorithm, a few definitions have to be presented for the different elements of a feedforward, finite impulse response (FIR) adaptive control algorithm:

| | |
|---|---|
| Nx | number of reference sensors |
| Ny | number of output actuators |
| Ne | number of error sensors |
| $W_{i,j,iter}$ | adaptive filter between $i^{th}$ input sensor and $j^{th}$ output actuator, after <<iter>> iterations |
| $\Delta W_{i,j,iter}$ | modification to the $W_{i,j,iter}$ |
| $H_{j,m}$ | reference filter modeling the path between the $j^{th}$ actuator and the $m^{th}$ error sensor |
| Lw | length of the adaptive filters $W_{i,j,iter}$ |
| Lh | length of the filters $H_{j,m}$ |
| $X_{i,k}$ | vector of the Lh last samples at time k from the $i^{th}$ input sensor |
| $e_{m,k}$ | sample at time k from the $m^{th}$ error sensor |
| $error_{m,k}$ | residual error for the $m^{th}$ error sensor at time k (see eq. 5, 6) |
| $y_{j,k}$ | sample at time k at the $j^{th}$ actuator |
| $V_{i,j,m,k}$ | vector of Lw last samples of the ref. signal calculated by filtering $X_{i,k}$ with $H_{j,m}$ |
| u | scalar value, step size of the adaptation |
| $X_{i,k}{}^T =$ | $[x_{j,k-1h+1} \ldots xi,k]$ |
| $H_{j,m}{}^T =$ | $[h_{j,m,1h} \ldots hj,m,1]$, |
| $W_{i,j,iter}$ | $[w_{i,j,iter,1w} \ldots wi,j,iter,1]$, |
| $V_{i,j,m,k}$ | $[v_{i,j,m,k-1w+1} \ldots vi,j,m,k]$, |

The basic equations of a multi-channel Filtered-X LMS are (<<*>> denotes a convolution product):

$$y_{j,k} = \sum_i X_{i,k}^T * W_{i,j,iter} \quad \text{(eq. 1)}$$

$$v_{i,j,m,k} = X_{i,k}^T * H_{j,m}, \quad \text{(eq. 2)}$$

$$W_{i,j,iter+1} = W_{i,j,iter} - u \sum_m V_{i,j,m,k} e_{m,k} \quad \text{(eq. 3)}$$

Equations 1, 2, and 3 are the multi-channel Filtered-X LMS algorithm.

Figure 4:
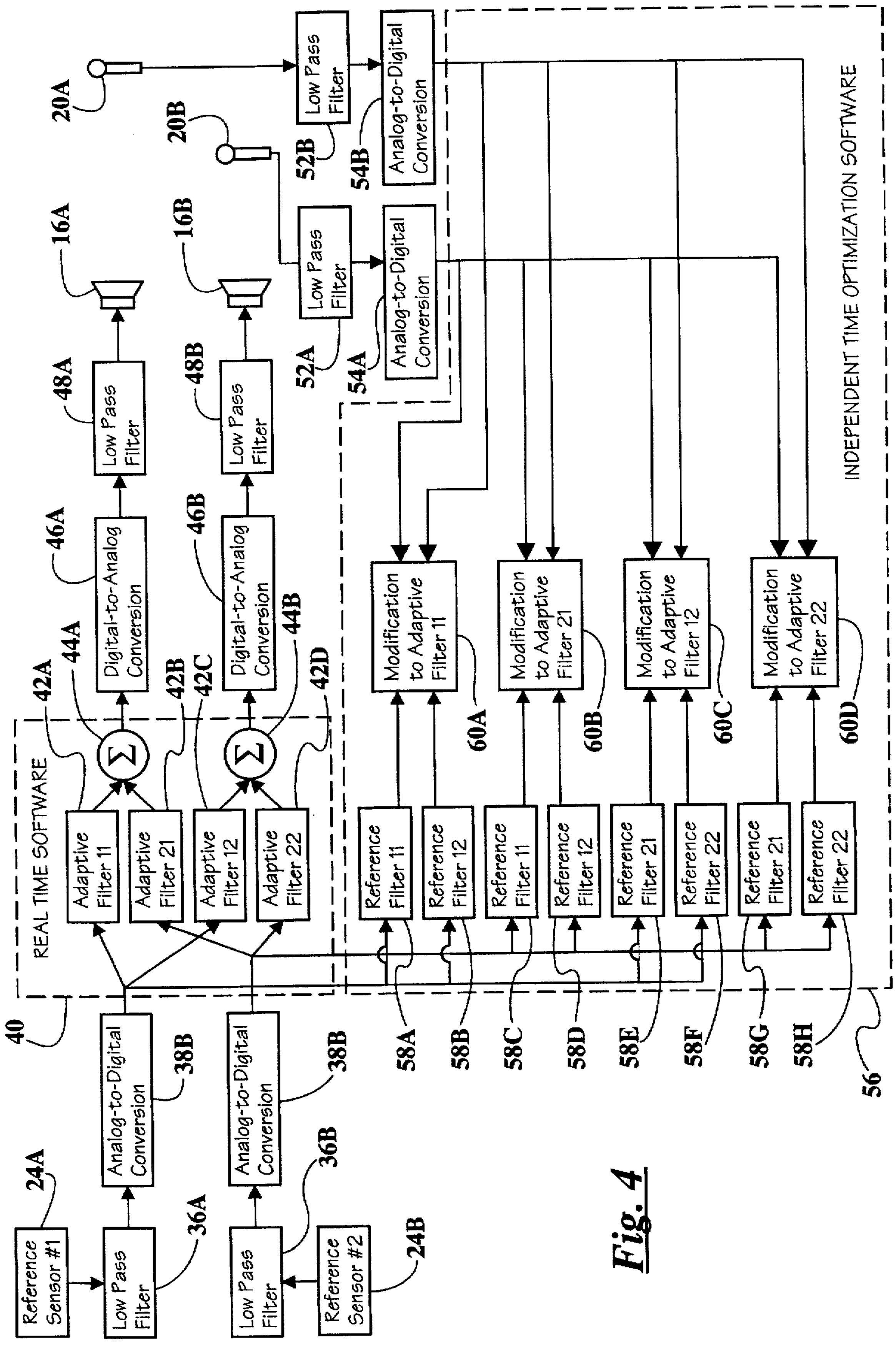
FIG. 4 is a schematic diagram showing the operation of a controller which comprises a component of the active noise control apparatus of FIG. 3.

FIG. 4 is a flow chart illustrating the FIR feedforward control structure used. It shows a system with 2 reference sensors, 2 output actuators and 2 error sensors.

In a real-time application, it is often useful (if not necessary) to separate the algorithm into two parts: a real time control part and an independent time optimization part. This separation is done to make possible the use of a multi-channel controller with a single digital signal processor. The real time part has to be calculated at each sample in the process, while the independent time part can be calculated during idle processor time. With this separation of the algorithm, $W_{i,j,iter}$ will not be modified at each sample and the optimization process will optimize the modifications filters $\Delta W_{i,j,iter}$ that should be added to the real time filter $W_{i,j,iter}$ in order to achieve the optimal performance:

$$W_{i,j,iter+1} = W_{i,j,iter} + \Delta W_{i,j,iter}. \text{ } (\Delta W_{i,j,iter} \text{ is then reset to 0 to start a new optimization cycle}) \quad \text{(eq. 4)}$$

The only equation that is calculated in real time is equation 1: the computation of the actuator values. With the separation of the algorithm, equation 2 remains valid for the computation of the filtered references, but equations 3 and 4 must be re-written:

$$\text{error}_{m,k} = \sum_{i}\sum_{i} V^{T}_{i,j,m,k} * \Delta W_{i,j,iter} + e_{m,k} \quad \text{(eq. 5)}$$

$$\Delta W_{i,j,iter+1} = \Delta W_{i,j,iter} - u \sum_{m} V_{i,j,m,k}\text{error}_{m,k}. \quad \text{(eq. 6)}$$

FIG. 4 is a flow chart illustrating the operation of the controller 28. For ease of understanding, the controller 28 shown in FIG. 4 is a two-channel controller, though it will be understood that the underlying principles apply equally to controllers having more channels. The output signals from each of the two reference sensors 24A, 24B are sent through corresponding low pass filters 36A, 36B and then through analog-to-digital converters 38A, 38B. The digital signals output from the analog-to-digital converters 38A, 38B are then input into a "real time software" section 40 of the controller 28. The real time software section 40 comprises adaptive filters 42A–D. The adaptive filters 42A–D are labeled in the format "adaptive filter ij" where i refers to the reference signal and j refers to the actuator signal. Thus adaptive filter 11, indicated by the reference numeral 42A, is a control filter which uses the output signal from the first reference sensor to produce an output signal to the first speaker; adaptive filter 21, indicated by the reference numeral 42B, uses the output signal from the second reference sensor to produce an output signal to the first speaker; and so on.

The output signals from adaptive filters 42A and 42B are summed at node 44A, and the output signals from the adaptive filters 42C and 42D are summed at node 44B. The output signals from the summing nodes 44A, 44B are then input into digital-to-analog converters 46A, 46B. The resulting analog output signals are passed through low pass filters 48A, 48B, and the filtered analog signal is then input into the corresponding speakers 16A, 16B.

Meanwhile, the error sensing microphones 20A, 20B detect the corresponding noise levels at their respective positions. The analog signals from the microphones 20A, 20B are passed through low pass filters 52A, 52B and then to analog-to-digital converters 54A, 54B. The digital signals corresponding to the noise level at the respective microphones 20A, 20B are then input into an "independent time optimization" section 56 of the controller 28. The digital output signals from the analog-to-digital converters 38A, 38B are also input into the independent time optimization section 56. The processes executed in the independent time optimization section 56 are not executed in real time but rather are calculated during idle processor time, thereby reducing the demand on the microprocessor and permitting use of a controller having only a single microprocessor.

The independent time optimization section 56 of the controller 28 comprises eight reference filters 58A–H. Each of the reference filters 58A–H is labeled in the format "reference filter jm" where j refers to an actuator and m refers to an error sensor. Thus reference filters 11, indicated by the numerals 58A and 58C, are filters which model the transfer function between the first actuator 16A and the first error sensor 20A; reference filters 12, indicated by the numerals 58B and 58D, are filters which model the transfer function between the first actuator 16A and the second error sensor 20B; and so on.

The digital signal corresponding to the first reference sensor 24A is input into each of four reference filters 58A, 58B, 58E, and 58F. Likewise, the digital signal corresponding to the second reference sensor 24B is input into each of four reference filters 58C, 58D, 58G, and 58H. The digital output signals from the reference filters 58A, 58B are input to a block 60A. In addition, the digital output signals from the first and second microphones 20A, 20B are input to the block 60A. The coefficients of the adaptive filter in block 42A are then modified, depending upon the values of the four inputs 58A, 58B, 20A, and 20B. The filters in blocks 60B, 60C, and 60D operate in the same manner to modify the coefficients of the adaptive filters 42B, 42C, and 42D, respectively.

In the disclosed embodiment the primary noise source comprises a pair of fans. Since there are actually two primary noise sources, two reference sensors 24A, 24B are required. In the case of a perturbance consisting of a single primary noise source, only one reference sensor 24A is required. In such a case, the second reference sensor 24B, along with its associated low pass filter 36B and analog-to-digital converter 38B, may be eliminated. In addition, the adaptive filters 42B and 42D are eliminated, as are the reference filters 58B, 58D, 58F, and 58H. Finally the summing nodes 44A, 44B may be removed.

Conversely, it will be appreciated that if the perturbance sought to be attenuated comprises more than two primary noise sources, then additional reference sensors 24 must be provided, each of which requires its own series of low-pass filters, analog-to-digital converters, adaptive filters, and reference filters.

The disclosed embodiment employs a feedforward control loop to control the speakers 16. As will be appreciated by those skilled in the art, reference sensors 24 are essential for a feedforward type of control loop. However, control of the speakers can also be accomplished by a feedback control loop, in which case the reference sensors 24 are not necessary. Such feedback control loops are well-known to those skilled in the art and thus will not be explained herein.

The steps involved in determining the number and location of error sensors within the error sensors plane will now be explained. The first step in the process is to determine the highest frequency of the perturbance which must be abated, and the temperature of the environment within the duct. This determination can be made using conventional acoustical and temperature measuring equipment. The wavelength of the highest frequency at the measured temperature is now determined. For the example of a 320 Hz perturbance within a chimney having a minimum operating temperature of 80° C., the wavelength λ is calculated as follows:

$$\lambda = \frac{C(T^{\circ})}{f}$$

where C(T) is the sound of speed at the given temperature T° in degrees Celsius, given by:

$$C(T^{\circ}) \cong 331 * \sqrt{\frac{1+T^{\circ}}{273}} \text{ meters/sec}$$

In the example of a 320 Hz perturbance within a chimney having a minimum operating temperature of 80° C., the speed of sound is:

$$C(T^{\circ}) \cong 376 \text{ meters/sec}$$

Thus the wavelength is:

$$\lambda \cong 376/320 \text{ meters} \cong 1.18 \text{ meters}$$

Because the maximum distance $D_{MAX}$ between each error sensor and the limit of its zone of influence is optimally less than or equal to one-third of the wavelength, $$D_{MAX} \leq \frac{\lambda}{3},$$

$$D_{MAX} \leq \frac{1.18}{3},$$

$$D_{MAX} \leq 0.39 \text{ meters}$$

Therefore at 320 Hz and 80° C., the maximum distance between each error sensor and the limit of its zone of influence should be less than 0.39 meters.

At this point, any of several methods can be used to obtain an arrangement of the sensors in the error sensor plane which will satisfy the limitation of $D_{MAX}$ being less than or equal to 0.39 meters. One can apply simple geometrical considerations or put so many error sensors in the error sensors plane that meeting of this limitation is assured.

However, because each error sensor requires its own channel of the controller, and because each additional channel places additional demands on the controller processor, at some point additional sensors will adversely affect the ability of the controller to generate the proper output signals in a timely manner. Accordingly, it is desirable to determine the minimum number and location of error sensors which will satisfy the limitation of $D_{MAX}$ being less than or equal to one-third of the wavelength of the highest frequency to be controlled.

Optimization of the number and location of the error sensors in the disclosed embodiment is achieved by application of the k mean algorithm. The k mean algorithm is widely used in speech coding and was first presented in 1965 by Forgy. A more recent treatment of the k mean algorithm is found in Makhoul, J., et al., *Vector Quantization in Speech Coding*, PROCEEDINGS OF THE IEEE, Vol. 73, No. 11, Nov. 1985, pp. 1551–1588, which publication is incorporated herein by reference. Because the k mean algorithm is so widely described in the literature, it will be explained herein only briefly.

Figure 5:
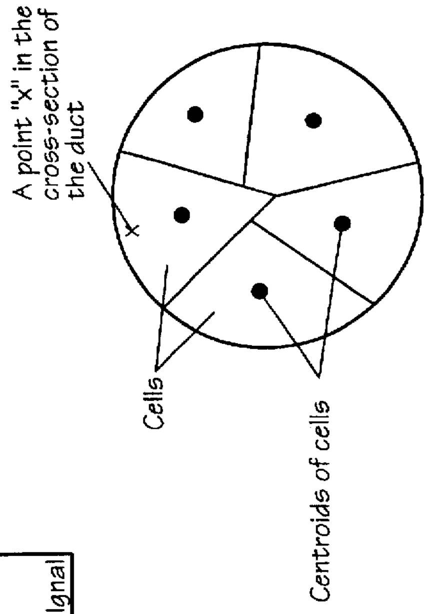
FIG. 5 is a diagram showing the application of the k mean algorithm to the duct of FIG. 3 to determine the optimum number and location of the error sensors.

In general terms, application of the k mean algorithm is described as follows. First, the following terminology will be used. The area of the cross section of the duct which is associated to an error sensor is called as a cell i. The error sensor associated with a cell i is located at the centroid Ci of the cell. FIG. 5 shows an example for five error sensors in a circular duct.

In Step 1 of the procedure, for the number L of cells considered, an initial value for the centroid vector $Y_i$ of the L cells is arbitrarily chosen in the overall cross section of the duct under consideration (the present example concerns a circle, but the approach is equally valid for a rectangle, a triangle, or any other shape). The order of iteration being m, this initial centroid vector is:

$$Y_i(m=0), \text{ for } 1<i<L$$

In Step 2 of the procedure, each point x in the cross-section of the error sensors plane is classified based on the nearest neighbor rule to determine to which centroid $Y_i$ each point x belongs:

$$x \in Ci(m), \text{iff}[d(x,Y_i(m))<d(x,Y_j(m))], \text{ all } j\neq i$$

where $d(x,Y_i(m)$ is the distance from the point x under consideration to the centroid $Y_i(m)$.

Step 3 is to recalculate the centroid of each cell, i.e., the error sensor's location, using the points associated to that cell:

$$Y_i(m+1)=Cent(Ci(m))$$

Finally, steps 2 and 3 are repeated until the location of the centroids $Y_i$ of the cells becomes stable.

The number and distribution of error sensors (microphones 20) in the error sensors plane 22 is such that it minimizes the maximum distance between each error sensor and the limit of its zone of influence in regard to the zone of influence of adjacent error sensors and of the walls of the duct. The minimum number of error sensors needed and their optimum locations in the error sensors plane is a function of the highest frequency of the noise which is to be controlled. In general, noise reduction will be obtained for frequencies having a wavelength greater than or equal to approximately three times the maximum distance from each error sensor and the limit of its zone of influence. Except for limitations which may be imposed by the capabilities of the controller 28, this noise reduction will be achieved for any type of noise, whether pure tone or wide band noise.

Applying this approach to the present example, a circular duct having a diameter of 1.8 meters, a perturbance of 320 Hz, and an operating temperature of 80° C., an arrangement of nine (9) error sensors will result in a $D_{MAX}$=0.40 meters, which is not sufficient. However, an arrangement of ten (10) error sensors yields a $D_{MAX}$=0.37 meters, which is less than 0.39 meters (the value calculated above for one-third of the wavelength at the given frequency and operating temperature). Thus in the case of a circular chimney having a perturbance of 320 Hz and an operating temperature of 80° C., a minimum of ten (10) error sensors should be used when located according to the k mean algorithm.

In addition, application of the k mean algorithm to the present example indicates that the ten sensors should be arranged with one sensor on the axis of the duct with the remaining nine sensors arranged in a ring-shaped formation concentric with the duct. More particularly, each of the nine sensors in the ring should be located 0.79 meters from the central axis of the duct, and the nine sensors should be equally spaced around the ring at 40° intervals.

Note that because this algorithm can be applied to ducts of any shape cross section (circle, rectangle, triangle, etc.), the k mean algorithm can be used to determine the optimum location of the error sensors in any duct shape.

Figure 6:
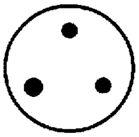
FIG. 6 is a table derived from the k mean algorithm which provides an alternate method for determining the optimum number and location of the error sensors.
Figure 6:
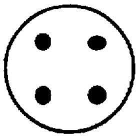
Figure 6:
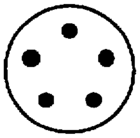
Figure 6:
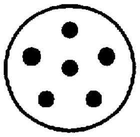
Figure 6:
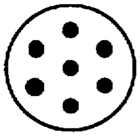
Figure 6:
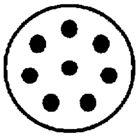
Figure 6:
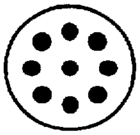
Figure 6:
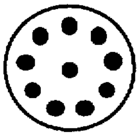
Figure 6:
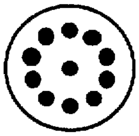
Figure 6:
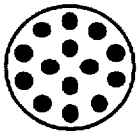

While application of the k mean algorithm indicates the optimum number and location of error sensors for a given duct cross-section, the iterative process is somewhat awkward. In a preferred embodiment, the ratio of $D_{MAX}/R_0$ ($R_0$ representing the radius of the duct) has been computed according to the k mean algorithm for various numbers of error sensors, and the ratios reduced to tabular format. FIG. 6 is a table which shows the ratio $D_{MAX}/R_0$ for various numbers of error sensors and the corresponding optimum location of the error sensors. Thus instead of using the k mean algorithm, this table can be consulted to determine the minimum number of microphones needed and their locations within the cross-section of a circular duct.

In the example under consideration, the diameter of the duct is 1.8 meters, and $R_0$ is thus 0.9 meters. The ratio of $D_{MAX}/R_0$ is thus 0.39/0.9, or 0.43. The table of FIG. 6 is thus consulted to find the largest $D_{MAX}/R_0$ which is less than 0.43. The table shows that an arrangement of ten (10) error sensors is the minimum number of sensors which will provide the desired attenuation of the perturbance. The table further indicates that the ten sensors are arranged with nine in a circular pattern and one sensor in the center of the duct. Further according to the table, the circular pattern of nine sensors is located at a radius R from the center of the duct wherein the ratio of $R/R_0$ is 0.71. In the present example, where $R_0$=0.9 meters, R=0.71/0.9=0.79 meters. Thus the circular pattern of nine sensors is located at a radius of 0.79 meters from the central axis of the duct. Also according to the table, $\Delta\phi$ for the optimum arrangement is 40°, meaning that each of the nine perimeter sensors is angularly offset by 40° from the preceding sensor.

Referring further to FIG. 6, it will be noted that beginning with fourteen (14) sensors, the error sensors are arranged in two rings. The second perimeter of sensors is located at radius R from the center of the duct which satisfies the listed ratio of $R/R_0$. In addition, the first sensor on the second perimeter of sensors is angularly offset from the first sensor on the first perimeter by an angle $\phi$, with each succeeding sensor in the second perimeter being offset by an additional angle $\Delta\phi$.

While the positioning of the error sensors within the error sensors plane is important if performance of the noise control system is to be optimized, positioning of the actuators, or speakers, is not critical. For the most part the speakers need not be located in any particular relation to the error sensors, to the other speakers, or to the duct. The speakers do not even need to be located within the same plane.

The only limiting factors of speaker placement to optimize performance are (1) to employ the same number of speakers as there are error sensors; (2) to position the speakers on the same side of the error sensors plane as the primary noise source or perturbance; and (3) to physically separate the speakers by at least a half wavelength of the lowest frequency to be controlled, to avoid acoustical redundancy, i.e., the fact that two speakers can appear to the microphones to be at nearly the same acoustical position, thereby reducing the efficiency of the controller to attenuate the noise at each error sensor. Note that these limitations still afford great latitude in terms of speaker location, since the speakers can be located between the primary noise source and the error sensors plane, on the side of the primary noise source opposite the error sensors plane, or even some speakers on one side of the primary noise source and other speakers on the opposite side.

The disclosed embodiment employs a feedforward control loop to control the speakers 16. As will be appreciated by those skilled in the art, reference sensors 24 are essential for a feedforward type of control loop. However, control of the speakers can also be accomplished by a feedback control loop, in which case the reference sensors 24 are not necessary.

While the disclosed embodiment is specifically directed toward a noise control apparatus for attenuating noise emanating from a chimney, it will be understood that the invention is by no means limited to chimneys and in fact is not even limited to industrial applications. Rather, the active noise control system of the present invention is suitable for any type of duct within which noise reduction is desirable.

Finally, it will be understood that the preferred embodiment has been disclosed by way of example, and that other modifications may occur to those skilled in the art without departing from the scope and spirit of the appended claims.

What is claimed is:

1. An apparatus for active noise control of high order modes in an undivided duct having a primary noise source, said apparatus comprising:

a plurality of error sensors located within the undivided duct in a plane which is perpendicular to the longitudinal axis of the duct;

a plurality of transducers disposed to direct sound waves into the duct, said plurality of transducers numbering at least as many as the number of said plurality of error sensors; and controller means responsive to an input signal from said plurality of error sensors for sending a control signal to said plurality of transducers to attenuate the noise within said duct generated by said primary noise source.

2. The apparatus of claim 1, wherein said plurality of error sensors are arranged within said plane such that the maximum distance from each of said sensors to the limit of the area under the influence of each of said sensors is less than or equal to one-third of the wavelength of the highest frequency noise sought to be attenuated.

3. The apparatus of claim 2, wherein the minimum number of error sensors necessary and the location of said error sensors within said plane is determined according to the k mean algorithm.

4. A method for active noise control of high order modes in an undivided duct having a primary noise source, comprising the steps of:

positioning a plurality of error sensors within said undivided duct in a plane perpendicular to the longitudinal axis of said duct;

positioning a plurality of transducers disposed to direct sound waves into the duct, said plurality of transducers numbering at least as many as the number of said plurality of error sensors; and responsive to an input signal from said plurality of error sensors, sending a control signal to said plurality of transducers to attenuate the noise within said duct generated by said primary noise source.

5. The method of claim 4, wherein said step of positioning a plurality of error sensors within said duct in a plane perpendicular to the longitudinal axis of said duct comprises the steps of:

determining the wavelength of the highest frequency of the noise within said duct which is sought to be attenuated;

arranging said plurality of error sensors within a plane perpendicular to the longitudinal axis of said duct such that the maximum distance from each of said sensors to the limit of the area under the influence of each of said sensors is less than or equal to one-third of the wavelength of the highest frequency noise sought to be attenuated.

6. The method of claim 5, wherein said step of arranging said plurality of error sensors within a plane perpendicular to the longitudinal axis of said duct such that the maximum distance from each of said sensors to the limit of the area under the influence of each of said sensors is less than or equal to one-third of the wavelength of the highest frequency noise sought to be attenuated comprises the steps of:

(a) for a number L of cells considered, arbitrarily choosing an initial value for the centroid vector $Y_i$ of the L cells in a cross section of the duct;

(b) the order of iteration being m, calculating this initial centroid vector according to the formula $Y_i(m=0)$, for $1<i<L$;

(c) recalculating the centroid of each cell using the points associated to that cell, according to the formula $Y_i(m+1)=Cent(Ci(m))$;

(d) repeating steps (b) and (c) until the location of the centroids $Y_i$ of the cells becomes stable;

(e) if the centroids $Y_i$ of the cells thus determined do not satisfy the limitation that the maximum distance from each of said centroids to the boundary of the cell associated with that centroid is less than or equal to one-third of the wavelength of the highest frequency noise sought to be attenuated, then repeat steps (a) through (d) with a larger number L of cells considered; and (f) once a number and configuration of centroids has been determined according to steps (a) through (e) which satisfies the limitation that the maximum distance from each of said centroids to the boundary of the cell associated with that centroid is less than or equal to one-third of the wavelength of the highest frequency noise sought to be attenuated, then positioning an error sensor at the centroid of each cell.

7. An apparatus for active noise control of high order modes in a duct having a primary noise source, said apparatus comprising:

a plurality of error sensors located within the duct in a plane which is perpendicular to the longitudinal axis of the duct;

a plurality of transducers disposed to direct sound waves into the duct, said plurality of transducers numbering at least as many as the number of said plurality of error sensors;

said plurality of error sensors and said plurality of transducers being arranged such that each of said plurality of error sensors receives sound waves from each of said plurality of transducers; and controller means responsive to an input signal from said plurality of error sensors for sending a control signal to said plurality of transducers to attenuate the noise within said duct generated by said primary noise source.

8. The apparatus of claim 7, wherein said plurality of error sensors are arranged within said plane such that the maximum distance from each of said sensors to the limit of the area under the influence of each of said sensors is less than or equal to one-third of the wavelength of the highest frequency noise sought to be attenuated.

9. The apparatus of claim 8, wherein the minimum number of error sensors necessary and the location of said error sensors within said plane is determined according to the k mean algorithm.

10. A method for active noise control of high order modes in a duct having a primary noise source, comprising the steps of:

positioning a plurality of error sensors within said duct in a plane perpendicular to the longitudinal axis of said duct;

positioning a plurality of transducers disposed to direct sound waves into the duct, said plurality of transducers numbering at least as many as the number of said plurality of error sensors;

said plurality of error sensors and said plurality of transducers being positioned such that each of said plurality of error sensors receives sound waves from each of said plurality of transducers; and responsive to an input signal from said plurality of error sensors, sending a control signal to said plurality of transducers to attenuate the noise within said duct generated by said primary noise source.

11. The method of claim 10, wherein said step of positioning a plurality of error sensors within said duct in a plane perpendicular to the longitudinal axis of said duct comprises the steps of:

determining the wavelength of the highest frequency of the noise within said duct which is sought to be attenuated;

arranging said plurality of error sensors within a plane perpendicular to the longitudinal axis of said duct such that the maximum distance from each of said sensors to the limit of the area under the influence of each of said sensors is less than or equal to one-third of the wavelength of the highest frequency noise sought to be attenuated.

12. The method of claim 11, wherein said step of arranging said plurality of error sensors within a plane perpendicular to the longitudinal axis of said duct such that the maximum distance from each of said sensors to the limit of the area under the influence of each of said sensors is less than or equal to one-third of the wavelength of the highest frequency noise sought to be attenuated comprises the steps of:

(a) for a number L of cells considered, arbitrarily choosing an initial value for the centroid vector $Y_i$ of the L cells in a cross section of the duct;

(b) the order of iteration being m, calculating this initial centroid vector according to the formula $Y_i(m=0)$, for $1<i<L$;

(c) recalculating the centroid of each cell using the points associated to that cell, according to the formula $Y_i(m+1)=Cent(Ci(m))$;

(d) repeating steps (b) and (c) until the location of the centroids $Y_i$ of the cells becomes stable;

(e) if the centroids $Y_i$ of the cells thus determined do not satisfy the limitation that the maximum distance from each of said centroids to the boundary of the cell associated with that centroid is less than or equal to one-third of the wavelength of the highest frequency noise sought to be attenuated, then repeat steps (a) through (d) with a larger number L of cells considered; and (f) once a number and configuration of centroids has been determined according to steps (a) through (e) which satisfies the limitation that the maximum distance from each of said centroids to the boundary of the cell associated with that centroid is less than or equal to one-third of the wavelength of the highest frequency noise sought to be attenuated, then positioning an error sensor at the centroid of each cell.

* * * * *